(12) United States Patent
Docherty et al.

(10) Patent No.: US 7,875,461 B2
(45) Date of Patent: Jan. 25, 2011

(54) TEST STRIP AND CONNECTOR

(75) Inventors: Edward Docherty, Inverness (GB); Mahyar Z. Kermani, Pleasanton, CA (US)

(73) Assignee: Lifescan Scotland Limited (GB)

( * ) Notice: Subject to any disclaimer, the term of this patent is extended or adjusted under 35 U.S.C. 154(b) by 771 days.

(21) Appl. No.: 11/782,548

(22) Filed: Jul. 24, 2007

(65) Prior Publication Data

US 2009/0029479 A1 Jan. 29, 2009

(51) Int. Cl.
*G01N 25/18* (2006.01)
*G01N 33/487* (2006.01)
*C12Q 1/58* (2006.01)
*G01N 27/00* (2006.01)
*G01N 27/26* (2006.01)

(52) U.S. Cl. ............. 436/149; 204/403.02; 204/403.03; 204/435; 422/50; 422/76; 422/82.01; 422/82.02

(58) Field of Classification Search ................. None
See application file for complete search history.

(56) References Cited

U.S. PATENT DOCUMENTS

| 5,653,918 | A | 8/1997 | Towlson |
| 5,708,247 | A | 1/1998 | McAleer et al. |
| 6,046,051 | A | 4/2000 | Jina |
| 6,179,979 | B1 | 1/2001 | Hodges et al. |
| 6,616,819 | B1 | 9/2003 | Liamos et al. |
| 6,749,740 | B2 | 6/2004 | Llamos et al. |
| 6,942,518 | B2 | 9/2005 | Liamos et al. |
| 2004/0225230 | A1 | 11/2004 | Liamos et al. |
| 2005/0096409 | A1 | 5/2005 | Davies |
| 2005/0161345 | A1 | 7/2005 | Groll et al. |
| 2006/0091006 | A1 | 5/2006 | Wang et al. |
| 2006/0191787 | A1 | 8/2006 | Wang et al. |
| 2006/0231417 | A1 | 10/2006 | Harding et al. |
| 2007/0110615 | A1 | 5/2007 | Neel et al. |

FOREIGN PATENT DOCUMENTS

| WO | WO 01/67099 A1 | 9/2001 |
| WO | WO 01/73124 A2 | 10/2001 |
| WO | WO 2004/039600 | 5/2004 |
| WO | WO 2004/039897 | 5/2004 |
| WO | WO 2004/040005 | 5/2004 |
| WO | WO 2004/040285 A1 | 5/2004 |
| WO | WO 2004/040287 A1 | 5/2004 |
| WO | WO 2004/040290 A1 | 5/2004 |
| WO | WO 2004/040948 A1 | 5/2004 |

*Primary Examiner*—Jill Warden
*Assistant Examiner*—Neil Turk

(57) ABSTRACT

An analyte test strip is provided that includes a generally planar substrate and a plurality of conductive areas disposed on the substrate to define five distinct conductive portions comprising at least five contact lands defining respective vertices of a polygon, and in which two contact lands are located in a single conductive portion. System and method utilizing the test strip are also described.

6 Claims, 6 Drawing Sheets

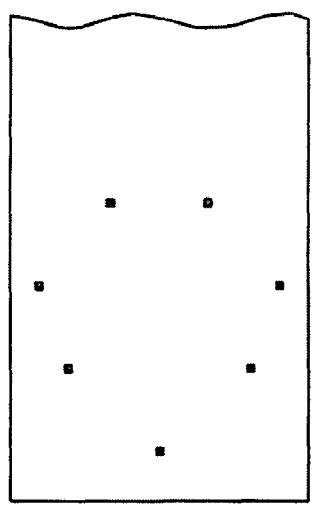
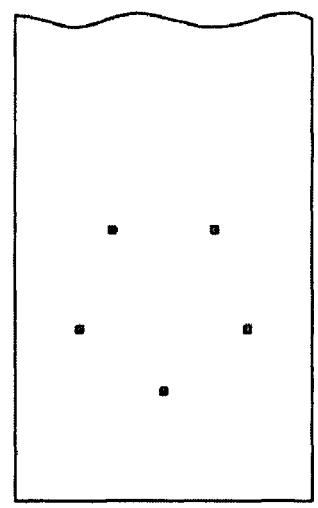
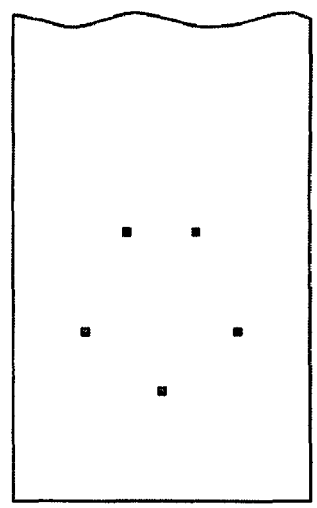
*FIG. 2A*    *FIG. 2B*    *FIG. 2C*

TEST STRIP AND CONNECTOR

BACKGROUND

Electrochemical methods and devices for determining analyte concentrations in fluid samples find wide application in the treatment and management of medical conditions such as diabetes. Individuals suffering from diabetes monitor their blood glucose concentrations using such methods often several times per day.

Electrochemical methods generally rely upon the correlation between a current, a potential or accumulated charge and the concentration of analyte, typically in conjunction with a reagent that produces charge carriers when combined with the analyte. The electrochemical biosensors for performing the tests are typically disposable test strips having a reagent disposed thereon that chemically reacts with a biological fluid such as blood. The test strip is mated to a test meter such that the test meter can measure the reaction between the analyte and the reagent to determine the concentration of the analyte. For electrochemically-based test strips, the electrical signal is transferred to the meter through electrical contact pads on the test strips and contacts within the meter strip port connector.

SUMMARY

In one aspect, an analyte test strip is provided that includes a generally planar substrate and a plurality of conductive areas disposed on the substrate to define five distinct conductive portions comprising at least five contact lands defining respective vertices of a polygon, and in which two contact lands are located in a single conductive portion.

In another embodiment, an analyte measurement system is provided that includes a housing and a test strip. The housing includes a connector module disposed in the housing. The connector module includes a plurality of spaced apart contact leads disposed in the connector module. The test strip includes a generally planar substrate. The test strip includes a plurality of conductive areas disposed on the substrate to define five distinct conductive portions having at least five contact lands defining respective vertices of a polygon, and in which two contact lands are located in a single conductive portions so that the plurality of spaced apart contact leads engages respective contact lands when the substrate is inserted into the connector module.

In yet a further embodiment, a method of operating a test measurement device is provided. The method can be achieved by providing a measurement device having seven contact leads; designating two contact leads as strip detection contact leads; and locating seven contact lands as respective vertices of a polygon on a substrate with two contact lands that are in substantial alignment with the strip detection contact leads when the substrate is inserted into the measurement device.

These and other embodiments, features and advantages will become apparent to those skilled in the art when taken with reference to the following more detailed description of the invention in conjunction with the accompanying drawings that are first briefly described herebelow.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which:

FIGS. 2A-2C are top views of strip port connector landing area configurations according to exemplary embodiments;

DETAILED DESCRIPTION

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1A:
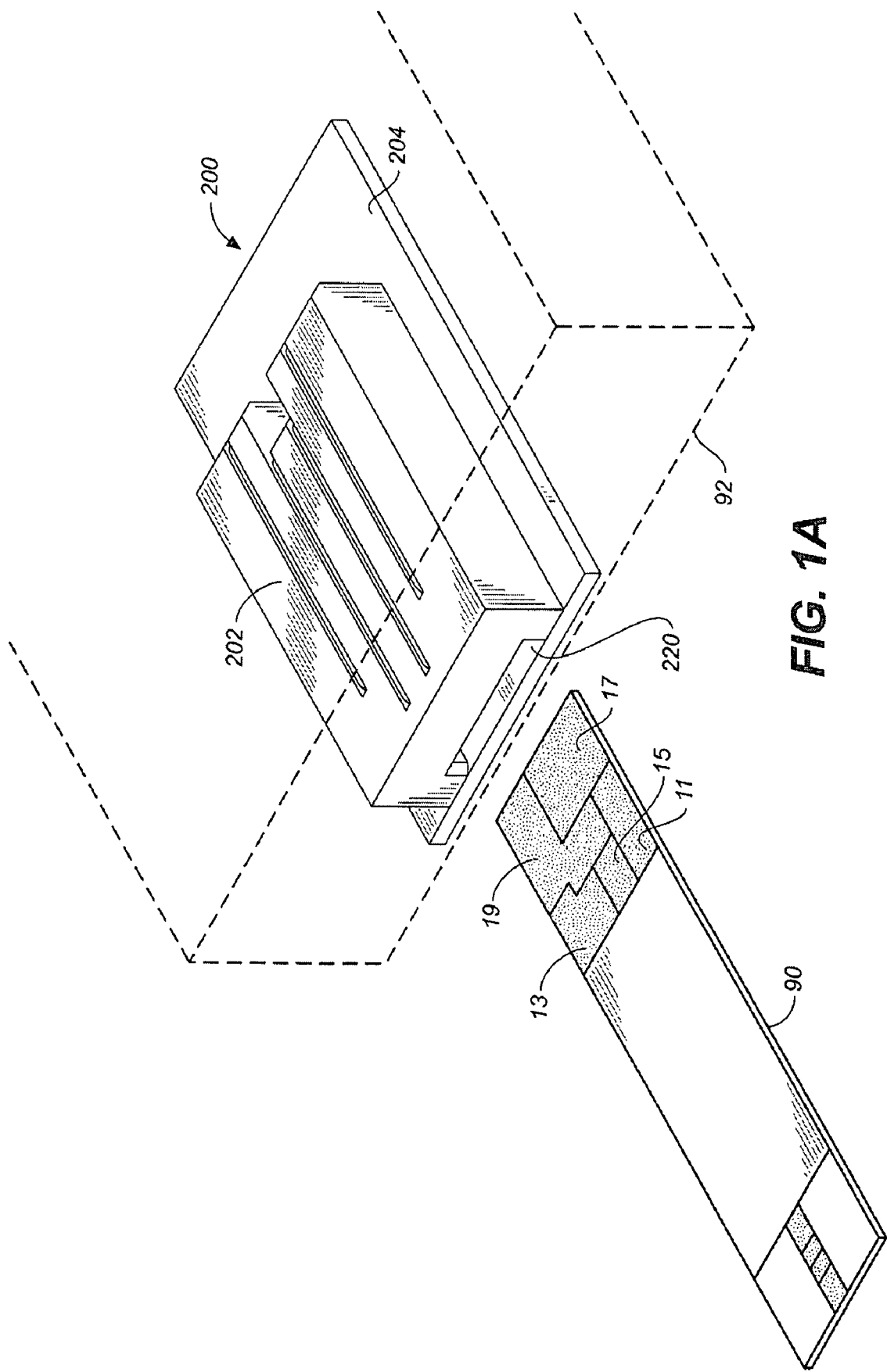
FIG. 1A is a top perspective view of the test strip system with a test strip positioned for insertion within an electrical connector device of a test meter.
Figure 1B:
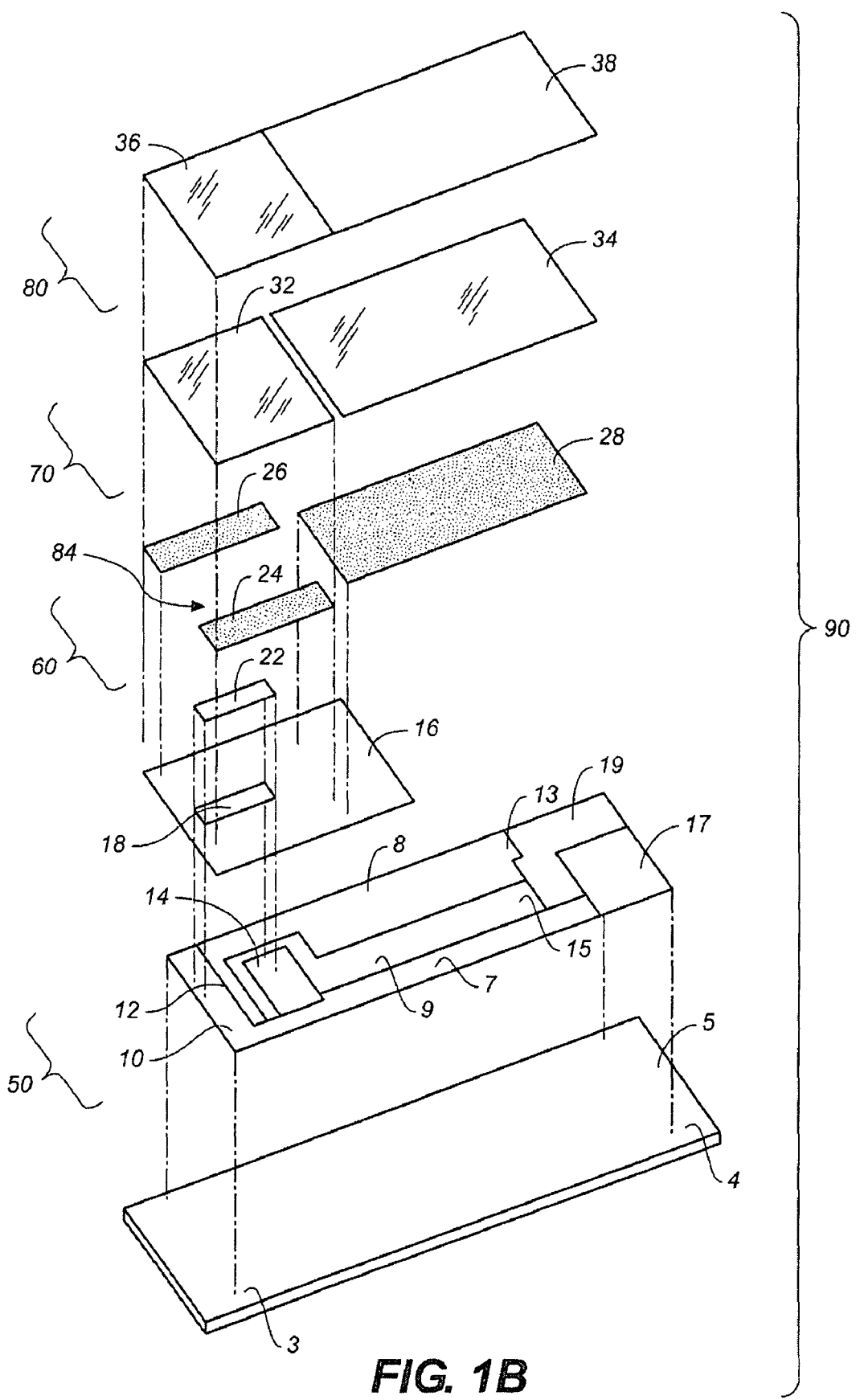
FIG. 1B is a top exploded perspective view of a test strip shown in FIG. 1A.
Figure 3A:
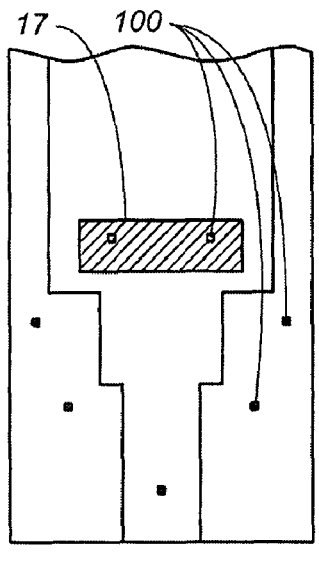
FIGS. 3A-3F are top views of the connector pad portion of strips according to exemplary embodiments with the strip port connector landing area configurations superimposed thereon.
Figure 3B:
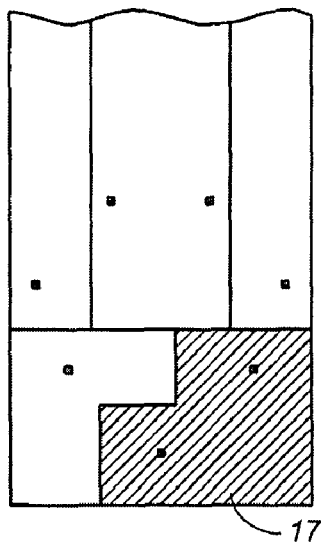
Figure 3C:
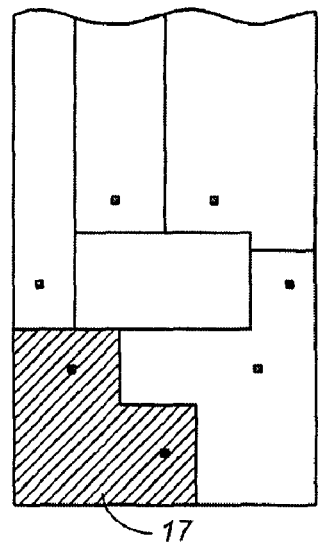
Figure 3D:
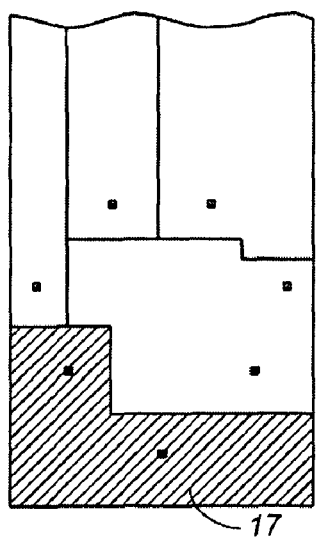
Figure 3E:
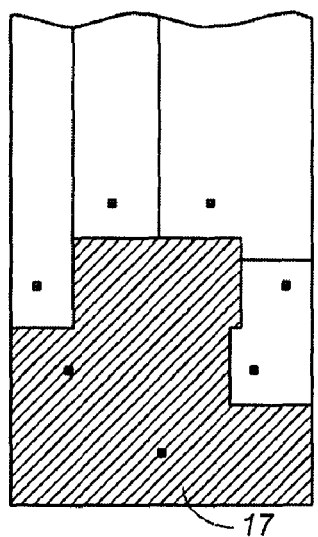
Figure 3F:
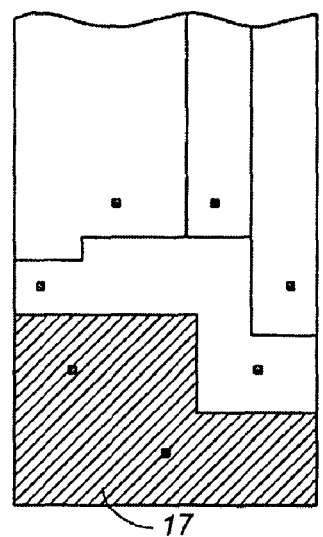
Figure 4A:
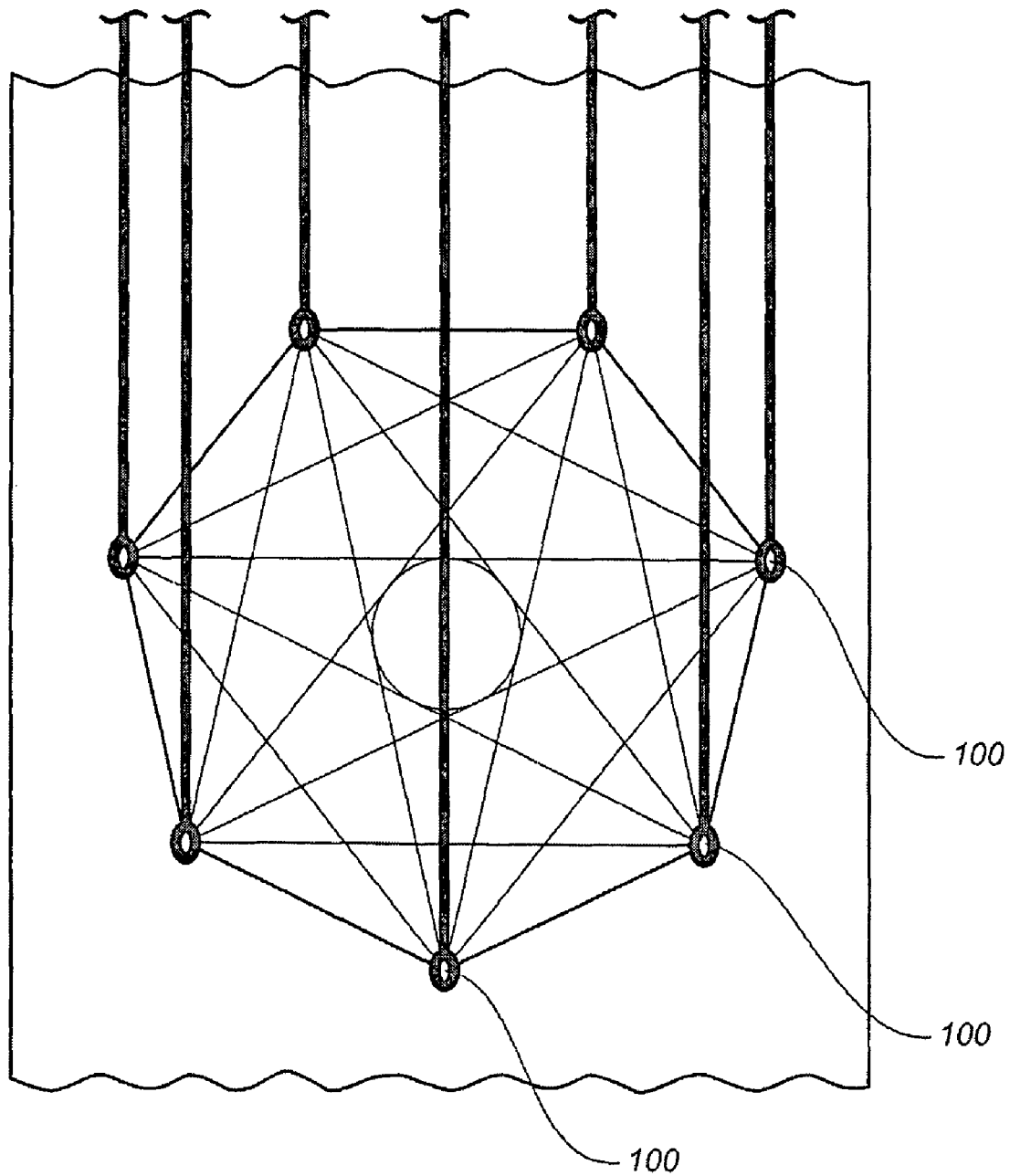
FIG. 4A illustrates the number of electrical interconnections possible by defining the contact lands on a test strip as respective vertices of a polygon on the test strip of FIGS. 1A, and 3A-3F.
Figure 4B:
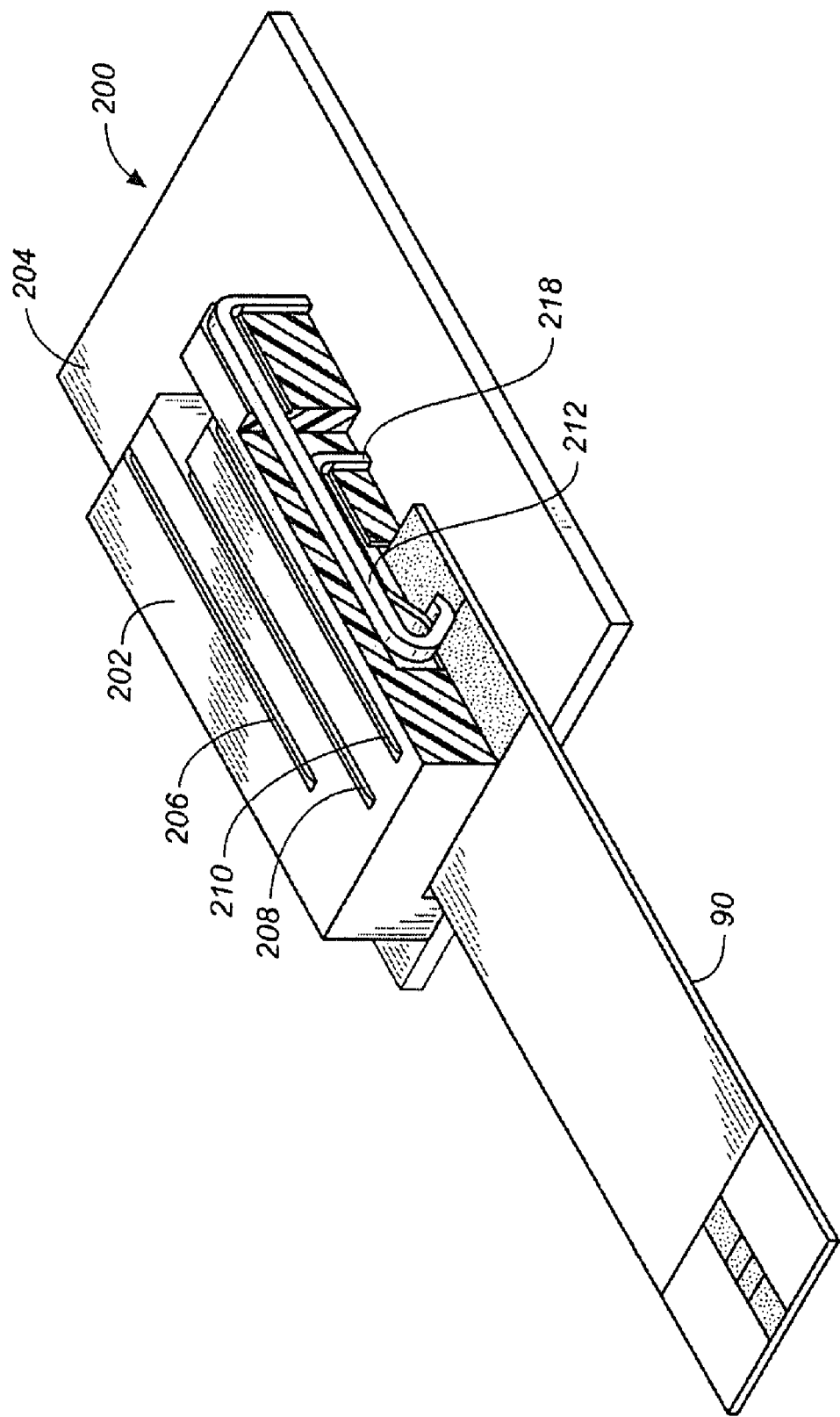
FIG. 4B is a top perspective view of the test strip shown in FIGS. 1A and 1B fully inserted within an electrical connector device.

Referring generally now to FIGS. 1A and 4B, test strip 90 shown in FIGS. 1A and 1B is typically coupled to a meter 92 or other electrical device by an electrical connector module 200, which is configured to couple with and contact the end of test strip 90 at contact pads 11, 13, 15, 17 and 19. In particular, the contact pads 11, 13, 15, 17, and 19 define five distinct conductive portions which may have at least five contact lands 100 (FIG. 3A) defining respective vertices of a polygon on a generally planar surface of test strip 90, and in which two contact lands are located in a single conductive portion. By this arrangement, the plurality of spaced apart contact leads (206, 208, 210, 212, 214) of the connector module 200 engages respective contact lands 100 (FIGS. 3A and 4A) when the test strip is inserted into the connector module 200 of the meter 92.

The meter 92 typically includes a potentiostat or other component to provide a potential and/or current for the electrodes of test strip 90. The meter 92 also typically includes a processor (e.g., a microprocessor or logical processing hardware) for determining analyte concentration from the test strip signals. The meter 92 may also include a display for displaying results determined from the test strip signals including, for example, analyte concentration, rate of change of analyte concentration, and/or the exceeding of a threshold analyte concentration (indicating, for example, hypo- or hyperglycemia).

Connector 200 is generally a two-part structure, having a first member 202 and a second member 204 (see FIG. 1A). Positioned between and secured by first member 202 and second member second member 204 are contact leads 206, 208, 210, 212, 214, 216 and 218 that provide electrical connection between test strip 90 and a meter. These leads 206, 208, 210, 212, 214, 216 and 218 have terminal ends to physically contact pads 11, 13, 15, 17, and 19 (shown in FIGS. 1A and 1B) and distal ends to connect to second member 204. Proximal end 5 of test strip 90 which has the contact pads can be slid into or mated with connector 200 by placing test strip 90 into a slide area (not shown), which provides a support for and retains test strip 90. The contact structures of connector 200 make electrical contact with the correct pads of the sensor so that the working electrode and counter electrode(s) are correctly coupled to the meter.

Leads 206, 208, 210, 212, 214, 216 and 218 may be parallel, non-overlapping and run longitudinally from their distal end to their terminal end. Leads 206, 208, 210 and 212 end at their respective terminal ends, but leads 214, 216 and 218 continue longitudinally past the proximal end of leads 206, 208, 210 and 212. As described previously, the terminal ends of leads 206, 208, 210, 212, 214, 216 and 218 can be staggered such that the contact landing areas form a polygon, e.g., a heptagon or a pentagon.

FIG. 1B is an exploded perspective view of a test strip 90, which includes multiple layers disposed upon a substrate 5. These layers may include a conductive layer 50, an insulation layer 16, a reagent layer 22, an adhesive layer 60, a hydrophilic layer 70, and a top layer 80. Test strip 90 may be manufactured in a series of steps wherein the conductive layer 50, insulation layer 16, reagent layer 22 and adhesive layer 60 are sequentially deposited on substrate 5 using, for example, a screen printing process as described in U.S. Pre-Grant Publication No. US20050096409A1 and published International Application No.'s WO2004040948A1, WO2004040290A1, WO2004040287A1, WO2004040285A2, WO2004040005A1, WO2004039897A2, and WO2004039600A2. In an alternative embodiment, an ink jetting process may be used to deposit reagent layer 22 on substrate 5. An exemplary ink jetting process is described in U.S. Pat. No. 6,179,979. Hydrophilic layer 70 and top layer 80 may be deposed from a roll stock and laminated onto substrate 5. In an alternative embodiment, a sputtering process is used to apply conductive layer 50 and patterns are created in conductive layer 50 by laser ablation. Test strip 90 includes a distal portion 3 and a proximal portion 4 as shown in FIGS. 1A and 1B.

The fully assembled test strip 90, as shown in FIG. 1B, includes an inlet 82 through which a blood sample may be drawn into a sample-receiving chamber 84. Inlet 82 may be formed by cutting through a distal portion 3 of test strip 90. A blood sample can be applied to inlet 82 to fill a sample-receiving chamber 84 so that glucose can be measured. The side edges of a first adhesive pad 24 and a second adhesive pad 26 located adjacent to reagent layer 22 each define a wall of sample receiving chamber 84. A bottom portion or "floor" of sample receiving chamber 84 includes a portion of substrate 5, conductive layer 50, and insulation layer 16. A top portion or "roof" of sample receiving chamber 84 includes distal hydrophilic portion 32.

For test strip 90, as shown in FIGS. 1A and 1B, conductive layer 50 includes a reference electrode 10, a first working electrode 12, a second working electrode 14, a reference contact pad 11, a first contact pad 13, a second contact pad 15, a strip detection contact pad 17 and an optional informational contact pad 19 (e.g., for calibration code information). Reference contact pad 11, first contact pad 13, second contact pad 15, strip detection contact pad 17 and informational contact pad 19 provide electrical connection to a test meter (denoted in FIG. 1A in dashed outline) to allow for data and measurement collection. In other embodiments, contact pad 17 may be informational and contact pad 19 may be used for strip detection.

Strip port connector electrical contact landing areas are shown in FIGS. 2A-2C. Strip port connector electrical contact landing areas may each be located at a vertex of a polygon. The polygon may have a regular or irregular shape with an odd number of vertices. Where the polygon is irregular in shape, its sides may not all have the same length or whose interior angles do not all have the same measure. In embodiments in which the polygon is regular in shape, the polygon is equilateral and equiangular. In one embodiment, the polygon is a heptagon (see FIG. 2A). In another embodiment, the polygon is a pentagon (see FIGS. 2B and 2C). Alternative embodiments of the contact portion of conductive layer 50 with the landing area for the strip port connector contacts superimposed thereon are shown in FIGS. 3A-3F. In FIGS. 3A-3F, the contact landing areas are each preferably located at the vertex of a heptagon. The shaded regions indicate the location of the strip detection pad that turns on the meter when test strip 90 is inserted therein. The strip detection pad is configured and arranged to close an electrical circuit between two contacts within the meter when test strip 90 is properly inserted into the meter. Proper insertion into the meter means that test strip 90 is inserted right side up, that the correct end of test strip 90 is inserted into the meter, and that test strip 90 is inserted far enough into the meter that reliable electrical connections are made between the electrodes contact pads and the corresponding contacts within the meter.

The arrangement of contact pads and strip port connector electrical contact-landing areas may be used to identify the geographical area in which the test strip may be used. If, for example, a customer inserts a test strip in a meter that does not have the correct configuration of contact pads and strip port connector electrical contact landing areas, then the meter will not be turned on or a test result will not be obtained.

Referring again to FIG. 1B, reference electrode 10, first working electrode 12 and second working electrode 14 are connected to reference contact pad 11, first contact pad 13, and second contact pad 15, respectively, by electrode extensions called "traces". The traces may be routed external to polygon, internal to polygon or may be routed both external and internal to polygon. First working electrode trace 8 provides an electrically continuous pathway from first working electrode 12 to first contact pad 13. Similarly, a second working electrode trace 9 provides an electrically continuous pathway from second working electrode 14 to second contact pad 15 and reference electrode trace 7 provides an electrically continuous pathway from reference electrode 10 to reference contact pad 11.

Suitable materials which may be used for the conductive layer are Au, Pd, Ir, Pt, Rh, stainless steel, doped tin oxide, carbon, and the like. In one embodiment, the material for the conductive layer may be a carbon ink such as those described in U.S. Pat. No. 5,653,918. In another embodiment, the material for the conductive layer may be a sputtered metal, and in particular a noble metal such as gold, palladium, or alloys thereof.

For test strip 90, insulation layer 16 includes aperture 18 that exposes a portion of reference electrode 10, first working electrode 12, and second working electrode 14, all of which can be wetted by a liquid sample. For example, insulation layer 16 may be Ercon E6110-116 Jet Black Insulayer™ ink, which may be purchased from Ercon, Inc (Waltham, Mass.).

Reagent layer 22 may be disposed on a portion of conductive layer 50, substrate 5, and insulation layer 16 as shown in FIG. 1B. In an embodiment of the present invention, reagent layer 22 may include chemicals such as an enzyme, a mediator which selectivity react with glucose and a buffer for maintaining a desired pH. Examples of enzymes suitable for use in this invention may include either glucose oxidase or glucose dehydrogenase. More specifically, the glucose dehydrogenase may have a pyrroloquinoline quinone co-factor (abbreviated as PQQ and may be referred to its common name which is methoxatin). Examples of mediator suitable for use in this invention may include either ferricyanide or ruthenium hexamine trichloride ($[Ru^{III}(NH_3)_6]Cl_3$ which may also be simply referred to as ruthenium hexamine). Examples of buffers suitable for use in the present invention may include phosphate, citrate or citraconate. Examples of reagent formulations or inks suitable for use in the present invention can be found in U.S. Pat. Nos. 5,708,247 and 6,046,051; published international applications WO01/67099 and WO01/73124.

In one embodiment, the formulation may include a 200 mM phosphate buffer having a pH of about 7 and a ruthenium hexamine mediator concentration ranging from about 5% and greater, preferably ranging from about 10% and greater, and yet more preferably ranging from about 15% to about 20% (percentage based on weight of mediator/volume of buffer). The pH of around 7 was chosen because glucose oxidase has a sufficiently high activity at this pH when using ruthenium hexamine as a mediator. The upper range for ruthenium hexamine was based on its solubility. When the enzyme ink is formulated to have greater than a 20% ruthenium hexamine concentration, solid particles of ruthenium hexamine were present in reagent layer 22 which do not dissolve during testing. The presence of undissolved ruthenium hexamine is believed to cause a decrease in the test strip-to-test strip precision. When the enzyme ink is formulated to have less than a 15% ruthenium hexamine concentration, the magnitude of the test current values decreased with the concentration of ruthenium hexamine.

In one embodiment, the formulation may have an enzyme activity ranging from about 1500 units/mL to about 8000 units/mL. The enzyme activity range may be selected so that the glucose current does not depend on the level of enzyme activity in the formulation so long as the enzyme activity level is within the above stated range. The enzyme activity should be sufficiently large to ensure that the resulting glucose current will not be dependent on small variations in the enzyme activity. For instance, the glucose current will depend on the amount of enzyme activity in the formulation if the enzyme activity is less than 1500 units/mL. On the other hand, for enzyme activity levels greater than 8000 units/mL, solubility issues may arise where the glucose oxidase cannot be sufficiently dissolved in the formulation. Glucose oxidase may be commercially available from Biozyme Laboratories International Limited (San Diego, Calif., U.S.A.). The glucose oxidase may have an enzyme activity of about 250 units/mg where the enzyme activity units are based on an o-dianisidine assay at pH 7 and 25° C.

Optionally, reagent layer 22 includes a matrix material that aides in retaining the reagent layer 22 on the surface of conductive layer 50 in the presence of fluid sample and has both hydrophobic and hydrophilic domains. Useful matrix materials include hydrophilic clay, kaolin, talc, silicates, diatomaceous earth or silicas such as Cab-o-Sil® TS630 or Cab-o-Sil® 530 (Cabot Corporation, Boston, USA). While not wishing to be bound by any particular theory, it is believed that silica forms a gel network in the presence of the sample that effectively maintains the coating on the surface of the electrode. Other useful matrix materials include polymeric materials such as sodium alginate, polyethylene glycol, polyethylene oxide, polyvinyl alcohol, polyvinyl acetate, polymeric latex materials, polyethersulfones, acrylic and methacrylic acid polymers; polymers derived from starch, cellulose and other natural polysaccharides, polyamides or collagen. An example of a useful coating composition is disclosed in Example 1 of U.S. Pat. No. 5,708,247. Reagent layer 22 may also optionally include at least one stabilizing agent such as albumin, sucrose, trehalose, mannitol or lactose, an agent such as hydroxyethylcellulose to adjust the viscosity, an antifoam agent such as DC1500, and at least one wetting agent such as polyvinylpyrrilidone or polyvinyl acetate.

In exemplary embodiments, reagent layer 22 is applied as a generally even layer to the exposed surface of the electrodes. The thickness of reagent layer 22 prior to contacting the fluid sample can be about 50 microns and usually does not exceed 20 microns. To provide an effective coating on the surface of the electrode, the thickness of the layer can be less than about 5 microns and is usually not less than about 7 microns.

For test strip 90, adhesive layer 60 includes first adhesive pad 24, second adhesive pad 26, and third adhesive pad 28 as shown in FIG. 1B. In an embodiment of the present invention, adhesive layer 60 may comprise a water based acrylic copolymer pressure sensitive adhesive which is commercially available from Tape Specialties LTD, which is located in Tring, Herts, United Kingdom (part#A6435). Adhesive layer 60 is deposed on a portion of insulation layer 16, conductive layer 50, and substrate 5. Adhesive layer 60 binds hydrophilic layer 70 to test strip 90.

Hydrophilic layer 70 includes a distal hydrophilic portion 32 and proximal hydrophilic portion 34. In one embodiment, hydrophilic layer 70 is a polyester material having one hydrophilic surface such as an anti-fog coating, which is commercially available from 3M.

For test strip 90, top layer 80 includes a clear portion 36 and opaque portion 38 as shown in FIG. 1B. Top layer 80 is disposed on and adhered to hydrophilic layer 70. As a non-limiting example, top layer 80 may be a polyester. It should be noted that the clear portion 36 substantially overlaps distal hydrophilic portion 32, allowing a user to visually confirm that the sample-receiving chamber 84 is sufficiently filled. Opaque portion 38 helps the user observe a high degree of contrast between a colored fluid such as, for example, blood within the sample receiving chamber 84 and the opaque portion 38 of top layer 80.

It is believed that, given the large number of electrochemically-based test strips on the market, users might try to use a less expensive test strip in a meter that is not designed for that meter, which could lead to inaccurate test results. If a less expensive test strip gives accurate test results in a meter for which it is not designed, this could result in illegal third party importation of test strips.

As provided for by applicants herein, various embodiments can be utilized to ameliorate the above problem. Such embodiments would also reduce third party importation of test strips that are not intended to be used in an intended geographical region or regions.

Also, by virtue of the arrangement of odd number of vertices of 5 or greater in a polygon defined by the contact lands, the arrangement would allow for a sufficient number of connection points with the meter and test strip. That is, with reference to FIG. 4A, the spatial distribution of the vertices 100 can be used when selecting pairs of vertices for providing the meter switching functionality. Any pair of vertex connection points can be utilized without posing any compromise to the availability of the three remaining vertices (with a pentagonal polygon) to provide the working and reference electrode connections. Similarly for higher order odd-numbered polygons (for example a heptagon) any pair of connection vertices can be selected for the switching function and any other pair of vertices, such that, when joined, produce a circuit that is non-crossing with the first switch-pair, and thus can be selected for a second function, leaving the final three vertices still fully accessibly for the working and the reference electrodes. Further, the spatial distribution can most effectively be utilized by constraining the use of the interior of the polygon for the meter-switching functionality and the exterior of the polygon figure for the measurement circuitry. This ensures that there will be no conflict between the circuitry requirements and maximizes the versatility of the concept for the number of incompatible test-strip variations that can be generated. The spatial distribution of the polygon figure results in a clear open space in the center of the figure, regardless of the complexity of any devised switching regime. This clear space can be utilized for strip anti-counterfeit security features.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An analyte measurement system comprising:
    a test meter with a housing, the test meter including a connector module disposed in the housing, the connector module including a plurality of spaced apart contact leads disposed in the connector module, and providing potential and/or current to the contact leads and determining analyte concentration from test strip signals; and
    a test strip comprising a generally planar substrate, the test strip including a plurality of conductive areas disposed on the substrate to define five distinct conductive portions comprising at least five contact lands defining respective vertices of a regular polygon with an odd number of at least five sides, and in which two contact lands are located in a single conductive portion so that the plurality of spaced apart contact leads engage respective contact lands when the substrate is inserted into the connector module.

2. The system of claim 1, in which the regular polygon comprises a regular heptagon.

3. The system of claim 2, in which the generally planar substrate extends along a longitudinal axis to define a generally rectangular member, in which one of the vertices of the regular heptagon is located substantially on the longitudinal axis and the remainder of the vertices are symmetric about the longitudinal axis.

4. The system of claim 3, further comprising first and second working electrodes and reference electrode in electrical communication with respective conductive portions.

5. The system of claim 1, in which the connector module comprises first and second members with the plurality of contact leads located proximate the first and second members.

6. The system of claim 5, in which the plurality of contact leads comprise respective terminal ends that define vertices of the regular polygon.

* * * * *